United States Patent

Bu et al.

Patent Number: 5,776,056
Date of Patent: Jul. 7, 1998

[54] HEALTH SELF-CHECKING SYSTEM USING REMOTE CONTROLLER AND TELEVISION AND METHOD THEREOF

[75] Inventors: Jong-Uk Bu; Kwang-Kyun Jung, both of Seoul, Rep. of Korea

[73] Assignee: LG Electronics Inc., Seoul, Rep. of Korea

[21] Appl. No.: 498,466

[22] Filed: Jul. 5, 1995

[30] Foreign Application Priority Data

Jul. 5, 1994 [KR] Rep. of Korea ............... 1994-16017

[51] Int. Cl.⁶ ........................................................ A61B 5/02
[52] U.S. Cl. ........................... 600/301; 600/525; 600/523; 600/483
[58] Field of Search ............................. 128/633, 664, 128/670, 672, 691, 700, 710, 696, 903, 712, 904; 600/310, 473, 483, 485, 504, 513, 523, 509, 300, 525, 301

[56] References Cited

U.S. PATENT DOCUMENTS

| | | | |
|---|---|---|---|
| 3,530,236 | 9/1970 | Marko | 128/903 |
| 3,603,881 | 9/1971 | Thornton | 128/903 |
| 3,646,606 | 2/1972 | Buxton et al. | 128/903 |
| 3,793,626 | 2/1974 | Zambuto | 128/710 |
| 3,986,498 | 10/1976 | Lewis | 128/903 |
| 4,051,522 | 9/1977 | Healy et al. | 128/903 |
| 4,356,486 | 10/1982 | Mount | 128/903 |
| 4,675,656 | 6/1987 | Narcisse | 128/903 |
| 4,794,532 | 12/1988 | Leckband et al. | 128/710 |
| 4,804,950 | 2/1989 | Moon et al. | 128/710 |
| 4,858,125 | 8/1989 | Washizuka et al. | 600/301 |
| 4,958,645 | 9/1990 | Cadell et al. | 128/903 |
| 4,974,607 | 12/1990 | Miwa | 128/903 |
| 5,046,504 | 9/1991 | Albert et al. | 128/710 |
| 5,086,778 | 2/1992 | Mueller et al. | 128/710 |
| 5,301,680 | 4/1994 | Rosenberg | 128/903 |
| 5,417,222 | 5/1995 | Dempsey et al | 128/696 |
| 5,441,047 | 8/1995 | David et al. | 128/904 |
| 5,447,164 | 9/1995 | Shaya et al. | 128/710 |
| 5,464,012 | 11/1995 | Falcone | 128/696 |
| 5,515,847 | 5/1996 | Braig et al. | 128/664 |
| 5,522,396 | 6/1996 | Langer et al. | 128/696 |
| 5,564,429 | 10/1996 | Bornn et al. | 128/696 |

*Primary Examiner*—William E. Kamm
*Assistant Examiner*—Kennedy J. Schaetzle

[57] ABSTRACT

A health self-checking system using a remote controller and a television and a method thereof, capable of easily checking a user's health using a remote controller and a television by checking user's heart rate and R-wave form, which includes a health checking information detection circuit provided in a remote controller for detecting a health checking information of a user; and a health checking information analyzing circuit provided in a television for receiving a health checking information outputted from the health checking information detection circuit and for analyzing the received health checking information and a medical data previously stored in a data base of the television and for displaying the analyzed information on the screen of a television.

19 Claims, 3 Drawing Sheets

HEALTH SELF-CHECKING SYSTEM USING REMOTE CONTROLLER AND TELEVISION AND METHOD THEREOF

BACKGROUND OF THE INVENTION

1. Field of the Invention

The present invention relates to a health self-checking system using a remote controller and a television, and in particular to a method of operating the health self-checking system using a remote controller and a television which is, capable of checking a user's heart rate and R-wave form of an electrocardiogram using a heart rate sensor and an R-wave form sensor that are disposed in a remote controller and computing health checking information such as heart rate and an R-wave form by comparing the computed health checking information with medical data stored in television and displaying the compared result on the screen of the television.

2. Description of the Conventional Art

The need of health self-checking medical systems such as e.g., a tonometer and blood sugar level checker, has been increased as people have become more concerned with on their health. Particularly, for adults, it is very important to check his/her health and prevent various kinds geriatric diseases. However, most of health self-checking medical instruments do not have functions to efficiently analyze health checking information and to properly cope with the checked health problems using the checked information because only numeric data is given to a user, which is difficult for users to understand. Therefore, to efficiently analyze the checked information, the user's health characteristics, e.g., age, sex, weight, height, and etc., should be considered for correct analysis. In addition, in using of a handy-type tonometer, there should be provided an additional data comparison table that contain consultation data of medical experts for better analysis relating to the checked health information.

In addition, since most of conventional tonometer is equipped with a cuff, an air pump provided for supplying air to the cuff, a valve provided for controlling an air pressure therein, a control circuit provided for controlling the system thereof, and a display, they are relatively costly.

SUMMARY OF THE INVENTION

Accordingly, it is an object of the present invention to provide a health self-checking system using a remote controller and a television and a method operating the health self-checking system, which overcomes the problems encountered in the conventional health checking system.

It is another object of the present invention to provide a health self-checking system using a remote controller and a television and a method of operating thereof, capable of checking a user's health by computing a user's heart rate and R-wave form using a heart rate sensor and an R-wave form sensor, which are disposed in a remote controller and by comparing the computed health checking information such as heart rate and R-wave form with medical data stored in a television and by displaying the compared result on the screen of a television.

To achieve the objects of the present invention, there is provided a health self-checking system using a remote controller and a television and a method of operating the health self-checking system, which includes a health checking information detection circuit provided in a remote controller for detecting a health checking information of a user; and a health checking information analyzing circuit provided in a television for receiving a health checking information outputted from the health checking information detection circuit and for analyzing the received health checking information and a medical data previously stored in the data base of the television and for displaying the analyzed information on the screen of a television.

To achieve the objects of the present invention, there is provided a health self-checking method using a remote controller and a television, which includes the steps of a first step which computes a heart rate by computing a circulating blood amount using the amount of light reflected from a skin after a light having an infrared ray band width is penetrated into the skin of a user by a predetermined depth and detects an R-wave form of an electrocardiogram at a finger; a second step which computes a detection time difference between the heart rate signal and the R-wave form, which are obtained by the first step; and a third step which checks a user's health state by comparing a health checking information such as a maximum blood pressure, a minimum blood pressure, and the like with a medical data and displays the compared result on the screen of a television.

DETAILED DESCRIPTION OF THE INVENTION

Figure 1:
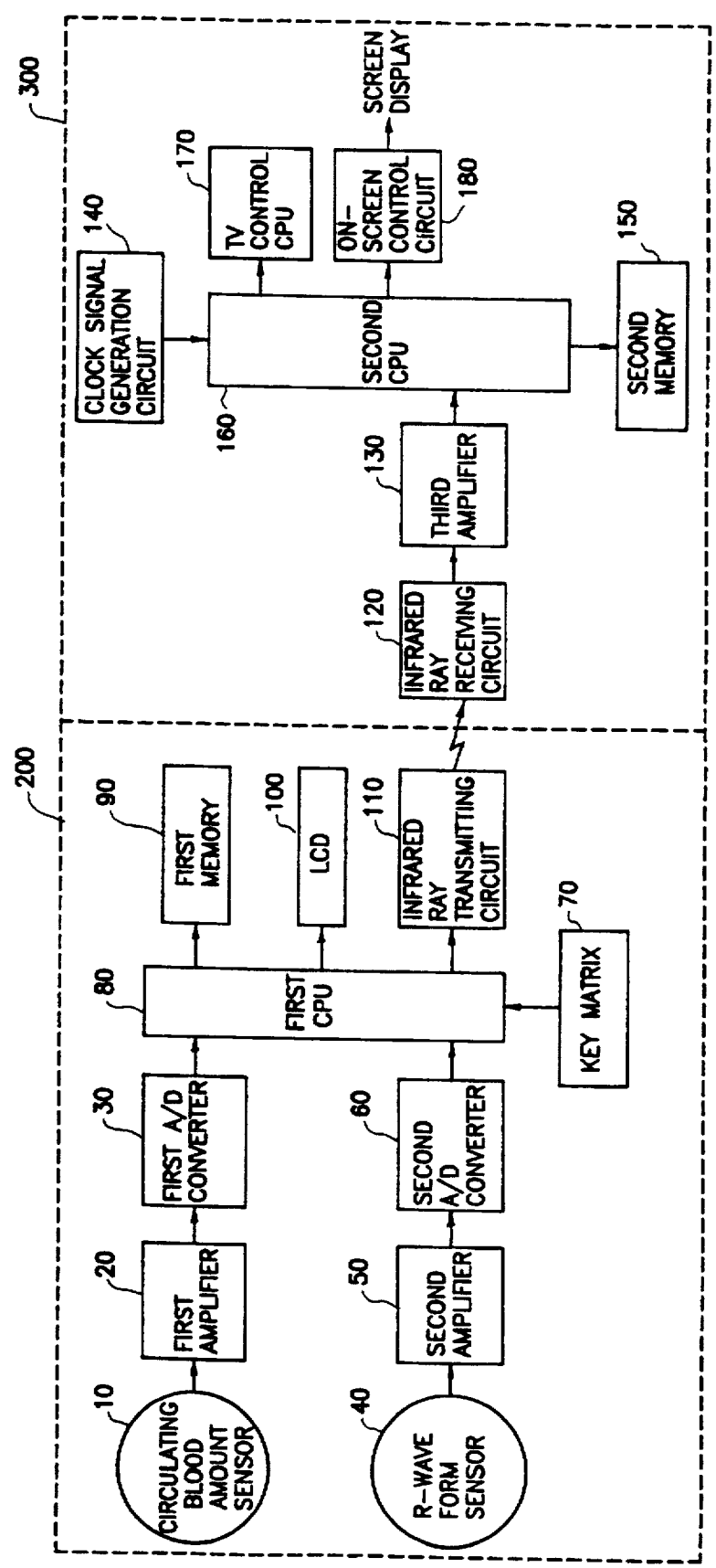
FIG. 1 is a block diagram of a health self-checking system using a remote controller and a television and a method thereof according to the present invention.

Referring to FIG. 1, a health self-checking system using a remote controller and a television and a method of operating the health self-checking system according to the present invention includes a health checking information detection circuit 200 provided in a remote controller for detecting a heart rate and R-wave form, and a health checking information analyzing circuit 300 provided in a television for analyzing the health checking information outputted from the health checking information detection circuit 200 and for displaying the analyzed health checking information on a screen of the television.

The health checking information detection circuit 200 includes a circulating blood amount sensor 10 provided for detecting a circulating blood amount of a user's finger, an R-wave form sensor 40 provided for detecting an R-wave form of an electrocardiogram of the user's finger, a first and second amplifiers 20 and 50 provided for amplifying a health checking information signal outputted from the circulating blood amount sensor 10 and the R-wave form sensor 40, first and second A/D converters 30 and 60 provided for converting an analog signal outputted from the first and second amplifiers 20 and 50 into a digital signal, a key matrix 70 provided for selecting a predetermined health checking mode, a first central processing unit 80 provided for computing a health checking information such as a maximum blood pressure, a minimum blood pressure, and a heart rate by logically operating the output data of the first and second A/D converters 30 and 60 in accordance with a predetermined health checking mode from the key matrix 70, a first memory 90 provided for storing a health checking information outputted from the first central processing unit 80, a liquid crystal display LCD 100 provided for displaying the health checking information outputted from the first central processing unit 80, and a health checking information analyzing circuit 300 provided for converting the health checking information outputted from the first central processing unit 80 into a transmittable signal.

The health checking information analyzing circuit 300 includes an infrared ray receiving circuit 120 provided for receiving the infrared signal outputted from the health checking detection circuit 200 and for converting the received signal into an electrical signal, a third amplifier 130 provided for amplifying the output signal of the infrared ray receiving circuit 120 by a predetermined level, a clock signal generating circuit 140 provided for generating a clock signal which is required to obtain an information on a current time, a second memory 150 provided for storing medical data to analyze with the health checking information, a second central processing unit 160 provided for storing the current time data from the clock signal generation circuit, data, and computed data value by analyzing health checking information outputted from the third amplifier 130 in real time using the medical data stored in the second memory 150, a television control central processing unit 170 provided for controlling the television operation in accordance with the key value of the second central processing unit 160, and an on-screen processing circuit 170 provided for displaying a health state, checked by the second central processing unit 160, on the screen of the television in accordance with a control of the television control central processing unit 160.

Figure 2:
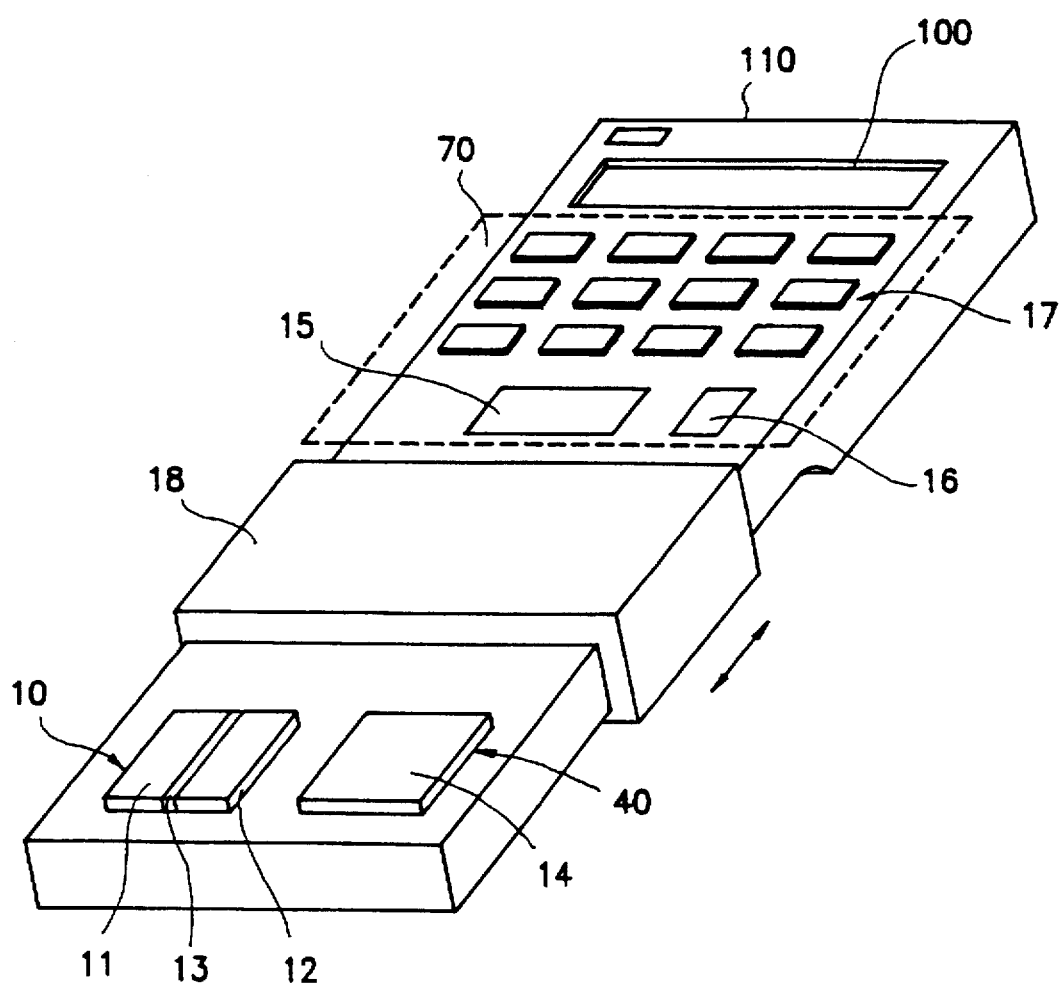
FIG. 2 is a perspective view showing of the remote controller adapted to the present invention.

Referring to FIG. 2, the circulating blood amount sensor 10 includes an LED 11 provided for generating a light so as to measure a circulating blood amount of the user's finger, a photo-transistor 12 provided for receiving a light reflected from the skin of the user's finger after a light outputted from the LED 11 is penetrated into the skin of the finger by a predetermined depth, a barrier 13 provided for separating the LED 11 and the photo-transistor 12, and an R-wave form detection electrode 14 provided for detecting an R-wave form outputted from the R-wave form sensor 40.

In addition, the key matrix 70 as shown in FIG. 2 includes a scroll bar 15 provided for selecting a desired health checking mode from the health checking menu an the screen of the television, an enter key 16 provided for starting the health-checking, and an operating key 17 provided for operating the television and a television channel selection and an audio volume control.

FIG. 2 shows a schematic remote controller according to the present invention, which includes a circulating blood amount sensor 10 having an LED 11, a photo-transistor 12, and a barrier 13, an R-wave form sensor 40 having an R-wave form detection electrode 14 provided for detecting an R-wave form of an electrocardiogram, a key matrix 70 having a scroll bar 15, an enter key 16, and an operation key 17, a cover 18 inserted onto the remote controller body for selectively covering a part of the upper surface of the remote controller in order to prevent the sensors from the outside environment, an LCD 100 provided for displaying a health checking information outputted from the first central processing unit thereon, and an infrared ray transmitting circuit 110 provided for converting a health checking information data outputted from the first central processing unit 80 into a transmittable information data.

The operation of the health self-checking system using a remote controller and a television and a method thereof according to the present invention will now be explained.

To begin with, a user puts one of his/her fingers of one hand on both the LED 11 and the photo-transistor 12 so as to compute his/her heart rate. In addition, when the user puts another finger of the same hand on the R-wave form detection electrode 14 of the R-wave form sensor 40, a light having an infrared ray wave length band penetrates into the skin of the finger of the user by a predetermined depth and then is reflected therefrom and advances to the photo-transistor 12.

At this time, hemoglobin in the user's blood receives a light having a certain wave length band of an infrared ray which is outputted from the LED 11.

Therefore, since the circulating blood amount varies in accordance with a heart rate, the number of hemoglobin in the blood varies. In addition, the incident amount of light by the photo-transistor 12 varies in accordance with an action of oxygen of the hemoglobin in the blood and causes the variation of voltage by the photo-transistor 12. The variation of the voltage is amplified by the first amplifier 20 by a predetermined level and is converted into a digital signal by the first A/D converter 30 and is outputted to the first central processing unit 80.

In addition, the R-wave form which is one of the R-wave forms in the electrocardiogram is detected by the R-wave form electrode 14 of the R-wave form sensor 40 and is amplified by the second amplifier 50 by a predetermined level and is converted into a digital signal by the first A/D converter 60 and is outputted to the first central processing unit 80.

In addition, in case of detecting a heart rate by using the circulating blood amount of the user's, due to the various kinds of reasons such as a shape of blood vessel, it takes relatively long time for the heart rate to reach the user's finger from the user's heart; however, in case of detecting an R-wave form, since it is detected very shortly after the extraction of the user's heart, a predetermined time difference occurs between the digital signal outputted from the first A/D converter 30 and the digital signal outputted from the second A/D converter 60.

Therefore, the first central processing unit 80 computes a time difference between the signal outputted from the first A/D converter 30 and the signal outputted from the second A/D converter 60, and computes the maximum blood pressure and the minimum blood pressure by comparing the computed time difference with the reference data, and computes a heart rate which is converted into a reference time by counting the heart rate for a predetermined time. In addition, the health checking information data such as the maximum blood pressure, the minimum blood pressure, and the heart rate are stored in the first memory 90.

In addition, the health checking information outputted from the first central processing unit 80 is displayed on the LCD 100 and is converted into an infrared ray by the infrared ray transmitting circuit 110 and is transmitted to the health checking information analyzing circuit 300 provided in the television.

The infrared ray receiving circuit 120 of the health checking information analyzing circuit 300, which is provided in the television, converts an infrared ray signal outputted from the infrared ray transmitting circuit 110 of the health checking information detecting circuit 200 into an electrical signal and outputs the converted signal to the third amplifier 130. The third amplifier 130 amplifies the signal applied thereto by a predetermined level and outputs the amplified signal to the second central processing unit 160.

At this time, the second central processing unit 160 controls the on-screen control circuit 180 and displays a health checking menu on the screen of a television. When a predetermined health checking mode is selected by the key matrix 70 of the remote controller, the data corresponding to the selected health checking mode is performed in real time based on the health checking information outputted from the third amplifier 130 using the medical data stored in the memory in accordance with the clock signal of the clock signal generation circuit 140 and outputs the performed data to the on-screen control circuit 180 after comprehensively checking and analyzing the health checking information. The analyzed health checking information is stored in the second memory at the current time.

In addition, the on-screen control circuit 180 displays the analyzed information on the screen of the television so that a user can check his/her health state.

The health checking menu described above according to the present invention includes a first mode which inputs and selects data such as user's identified number, date of birth, sex, weight, height, and the like; a second mode which measures a maximum blood pressure, a minimum blood pressure, and a heart rate; a third mode which stores and deletes a measured data; a fourth mode which analyzes the measured data using the data base and outputs the analyzed health checking information; a fifth mode which display a changed heath state on a screen in graphic; and a sixth mode which warns user to when a certain health symptom is checked as a result of an analysis of the health checking data.

Figure 3:
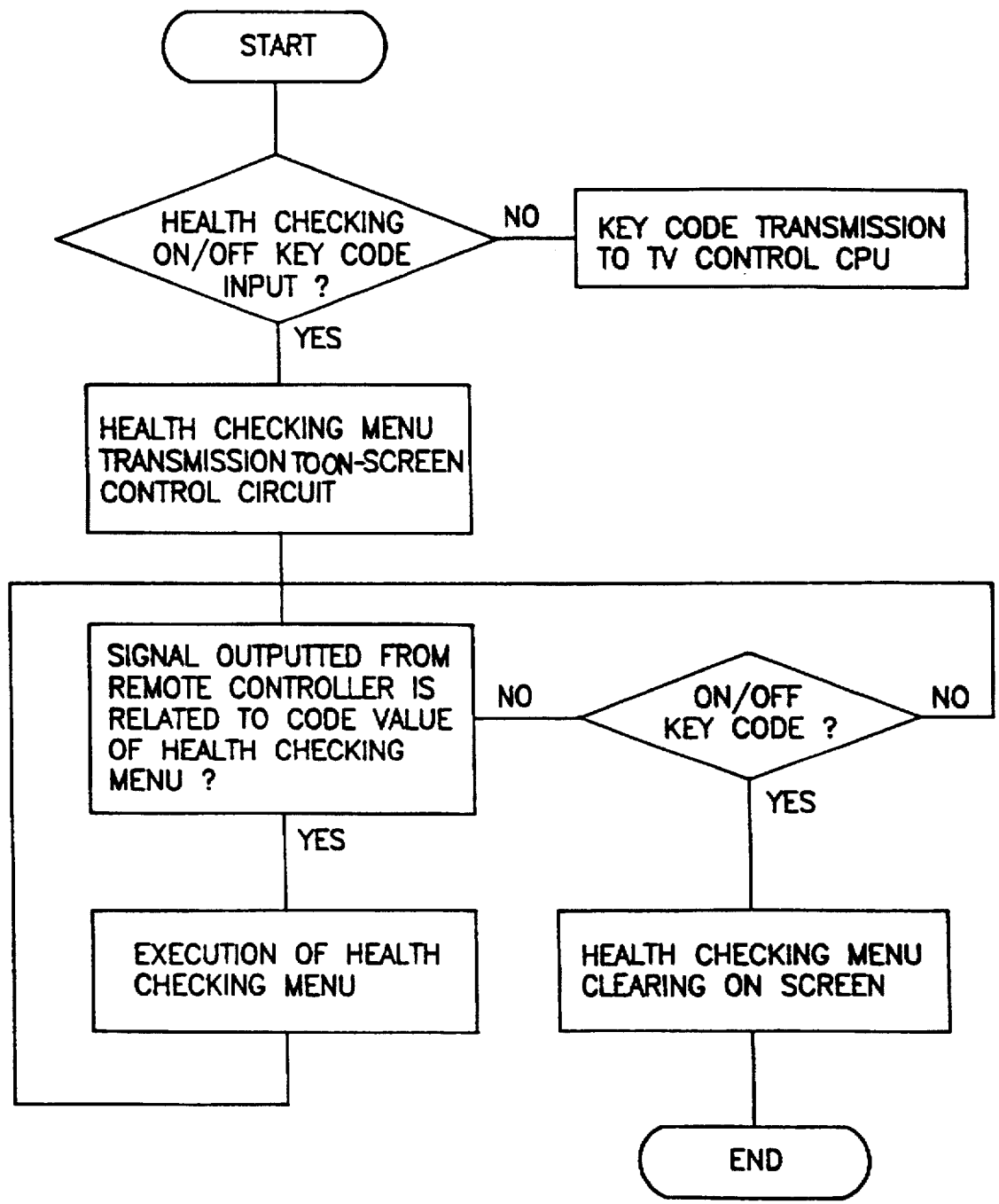
FIG. 3 is a flow-chart illustrating the operation of of FIG. 1 according to the present invention.

Referring to FIG. 3, the operation of each health checking mode will now be explained.

To begin with, the second central processing unit 160 detects whether a user selected a predetermined health checking mode, that is, checks whether a health checking on/off key is inputted.

At this time, when a predetermined health checking mode was inputted, the central processing unit 160 transmits the selected health checking mode to the on-screen processing circuit 180 so that the selected health checking mode is displayed on the screen of the television. When a predetermined health checking mode was not inputted, the second central processing unit 160 transmits a predetermined key value to the television control central processing unit 170. The television control central processing unit 170 controls the on-screen processing circuit 180 and displays a common television program(not the health checking information) on the screen of the television.

In addition, when the health checking menu is displayed on the screen of the television, the second central processing unit 160 judges whether a signal outputted from the remote controller is a code related to the selected health checking mode.

At this time, as a result of the above described judgement, when it is related to the health checking menu, the second central processing unit 160 performs a corresponding mode based on the health checking information outputted from the third amplifier 130 using the medical data base stored in the second memory 150. In addition, as a result of the above described judgement, when it is not related to the health checking menu, the second central processing unit 160 checks whether the signal outputted from the remote controller is a health checking on/off key code. As a result of above described check, when it is not an on/off key code, the second central processing unit 160 checks the next code signal outputted from the remote controller. As a result of above described check, when it is an on/off key code, the second central processing unit 160 clears the health checking menu displayed on the screen of the television and ends the operation.

In addition, to accomplish the present invention, it is not limited to the use of a heart rate and an R-wave form. For better accomplishments of the present invention, it is also possible to use methods of checking tiredness or blood sugar levels by analyzing sweat components using a bio-sensor and of using an advanced health checking system using fuzzy logic or chaos theories.

For examples, the present invention can be better accomplished by providing a network communication system between a hospital's medical data base or doctors (including herb doctors) and a user via a television and a remote controller with a health checking system.

As described above, a health self-checking system using a remote controller and television and method thereof according to the present invention capable of easily checking a user's health using a remote controller and a television by checking user's heart rate and R-wave form of an electrocardiogram.

What is claimed is:

1. A health self-checking system, comprising:
   a remote controller;
   a television unit for storing medical information;
   a health checking information detection circuit provided in the remote controller for detecting health checking information of a user and for outputting the detected health checking information; and
   a health checking information analyzing circuit provided in the television unit for directly receiving the health checking information outputted from the health checking information detection circuit, for analyzing the received health checking information with the medical information stored in the television unit, and for displaying user information based on the analyzed information on a screen of the television unit.

2. The system of claim 1, wherein the health checking information detection circuit includes:
   a first sensor for sensing an amount of circulating blood in a finger of the user and generating an output signal;
   a second sensor for sensing an R-wave form from the finger of the user that represents an electrocardiogram of the heart of the user and generating an output signal;
   first and second amplifying circuits for amplifying the output signals from the first sensor and the second sensor, respectively;
   first and second A/D converters for converting an analog signal outputted from each of the first and second amplifying circuits into a digital signal;
   a key matrix for selecting a health checking mode;
   a first central processing unit for computing health checking information of the user by processing the outputs of the first and second A/D converters in accordance with the selected health checking mode by the key matrix;
   a first memory for storing the health checking information outputted from the first central processing unit;
   a display for displaying the health checking information outputted from the first central processing unit; and
   a transmitting circuit for converting the health checking information outputting from the central processing unit into a transmittable signal and for outputting the transmittable signal from the remote controller to the health information analyzing circuit of the television unit.

3. The system of claim 2, wherein the health checking information analyzing circuit includes:
   a receiving circuit for converting the transmittable signal from the transmitting circuit into an electrical signal;

a third amplifying circuit for amplifying the output signal of the receiving circuit to a predetermined level;

a clock signal generating circuit for generating a clock signal relating to time information;

a second memory for storing the medical data used to analyze the health checking information;

a second central processing unit for processing the health checking information outputted from the third amplifying circuit with the medical data stored in the second memory based on the time information of the clock signal generating circuit to determine health state information; and an on-screen processing unit for processing the health state information outputted from the second central processing unit and for displaying the processed health state information on the screen of the television unit.

4. The system of claim 2, wherein the first sensor includes:

a light emitting diode (LED) for transmitting a light signal having an infrared ray band width to compute the amount of circulating blood in the finger of the user;

a photo-transistor for receiving a light reflected from the skin of the user; and a barrier for separating the LED and the photo-transistor.

5. The system of claim 2, wherein the second sensor includes an electrode that detects the R-wave form.

6. The system of claim 2, wherein the health checking mode includes:

a first mode for inputting and selecting at least one of a user's identified number, date of birth, sex, weight, and height;

a second mode for measuring a maximum blood pressure, a minimum blood pressure, and a heart rate and generating measured data thereof;

a third mode for storing and deleting the measured data;

a fourth mode for analyzing the measured data and for outputting the health checking information based on the analyzed measured data;

a fifth mode for displaying a changed health state on the display; and a sixth mode for indicating when a certain health symptom is checked positive as a result of the analyzed health checking information.

7. The system of claim 2, wherein the health checking information includes at least one of a maximum blood pressure, a minimum blood pressure, and a heart rate of the user.

8. The system of claim 2, wherein the remote controller includes:

a sliding cover for protecting the first and second sensors.

9. The system of claim 1, wherein said health checking information detection circuit further includes a bio-sensor for detecting sweat from a user which is used to compute tiredness and blood sugar level information of the user.

10. A self-check health system, comprising:

a television remote controller unit for detecting health characteristics from a user, and for processing the detected health characteristics into health information; and a display unit for receiving the health information, for analyzing the received health information to produce user information, and for displaying the user information based on the analyzed health information.

11. The system of claim 10, wherein the display unit is included in a television unit which is remotely controlled by the television remote controller unit.

12. The system of claim 10, wherein the television remote controller unit includes:

at least one sensor input for detecting a health characteristic; and a first processing unit for processing at least one detected health characteristic into the health information.

13. The system of claim 12, wherein the display unit includes:

a receiving unit for receiving the health information from the first processing unit;

a memory unit for storing medical data;

a second processing unit for processing the received health information with the medical data stored in the memory unit into the user information; and a display control for displaying the user information to a screen of the display unit.

14. The system of claim 10, wherein the television remote controller unit includes:

a plurality of inputs, each input generating signals; and a sliding protective cover for protecting at least one of the inputs.

15. A method for health self-checking using a television unit and a remote controller for controlling the television unit, comprising the steps of:

sensing at least one health characteristic from a user, each health characteristic is sensed by a corresponding sensor of the remote controller;

selecting a health checking mode using the remote controller;

computing health checking information by a first processing unit within the remote controller based on the selected health checking mode and the at least one health characteristic;

analyzing the computed health checking information by a second processing unit within the television unit with medical information stored in the television unit;

generating user information based on the analyzed information; and outputting the user information to a screen of the television unit.

16. The method of claim 15, wherein the step of sensing at least one health characteristic includes the steps of:

sensing an amount of circulating blood of the user by a first sensor of the remote controller; and sensing an R-wave form representing an electrocardiogram by a second sensor of the remote controller.

17. The method of claim 16, wherein the step of sensing at least one health characteristic further includes the step of:

sensing one of a blood sugar count and tiredness level by a third sensor of the remote controller.

18. The method of claim 15 further, including the step of:

controlling the television unit by a key matrix of the remote controller.

19. The method of claim 15, wherein the health checking information includes at least one of a heart rate and blood pressure health checking information.

* * * * *